United States Patent [19]

Quirk et al.

[11] Patent Number: 4,556,722

[45] Date of Patent: Dec. 3, 1985

[54] PROCESS FOR THE PREPARATION OF AMINOPROPYLALKOXYSILANES

[75] Inventors: Jennifer M. Quirk, Bedford Hills, N.Y.; Scot Turner, Marietta, Ohio

[73] Assignee: Union Carbide Corporation, Danbury, Conn.

[21] Appl. No.: 717,036

[22] Filed: Mar. 28, 1985

[51] Int. Cl.$^4$ ............................. C07F 7/08; C07F 7/10
[52] U.S. Cl. ................................................... 556/413
[58] Field of Search ........................................ 556/413

[56] References Cited

U.S. PATENT DOCUMENTS

| | | | |
|---|---|---|---|
| 2,762,823 | 9/1953 | Speier | 556/413 X |
| 3,527,809 | 9/1970 | Pruett et al. | 260/604 |
| 3,657,304 | 4/1972 | Holub et al. | 556/413 |
| 3,665,027 | 5/1972 | Reichel | 260/448 |
| 3,864,373 | 2/1975 | Seiler et al. | 260/448 |
| 4,148,830 | 4/1979 | Pruett et al. | 260/604 |
| 4,481,364 | 11/1984 | Chu et al. | 556/413 |

*Primary Examiner*—Paul F. Shaver
*Attorney, Agent, or Firm*—Daniel Reitenbach

[57] ABSTRACT

A process for the preparation of aminopropylalkoxysilanes comprising the hydrosilation of allylamines (including N-substituted allylamines) with alkoxyhydrosilanes in the presence of a rhodium-triorganophosphorus-complex catalyst. This process significantly increases the gamma- to beta-isomer ratio of the final product of the addition of allylamines to alkoxyhydrosilanes.

29 Claims, No Drawings

PROCESS FOR THE PREPARATION OF AMINOPROPYLALKOXYSILANES

FIELD OF THE INVENTION

This invention relates to a novel process for preparing aminopropylalkoxysilanes. More particularly, this invention relates to a process for hydrosilation of allylamines (including N-substituted allylamines) with alkoxyhydrosilanes in the presence of a rhodium-triorganophosphoruscomplex catalyst.

BACKGROUND OF THE INVENTION

Catalyzed additions of allylamines to alkoxyhydrosilanes are known methods for preparation of aminopropylalkoxysilanes. Of the known catalysts platinum catalysts have been shown to be the most useful for these reactions. These platinum-catalyzed reactions produce both gamma- and beta-isomers of the final product, e.g., a gamma- to beta-isomer ratio of up to about 15:1 has been described in U.S. Pat. No. 4,481,364. Since the gamma-isomer is the desirable isomer, the beta-isomer must be removed to obtain a relatively pure (>95%) product of the gamma-isomer. It would, therefore, be desirable to utilize a hydrosilation process which would effectively increase the ratio of gamma- to beta-isomer of the final product (e.g. the ratio of gamma-aminopropyltriethoxysilane to beta-aminopropyltriethoxysilane).

Accordingly, it is an object of this invention to provide a method for significantly increasing the gamma- to beta- isomer ratio of the final product of the addition of allylamines to alkoxyhydrosilanes.

DESCRIPTION OF THE INVENTION

This invention involves a novel process for the preparation of an aminopropylalkoxysilane having the formula

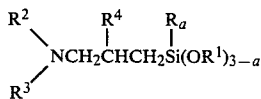

wherein R and $R^1$ individually are $C_1$–$C_6$ alkyl; $R^2$ and $R^3$ individually are hydrogen, $C_1$–$C_{10}$ alkyl, $C_1$–$C_{10}$ alkenyl, —$CH_2CH_2NHCH_2CH_2NH_2$, —$CH_2CH_2NH_2$, phenyl or substituted phenyl; $R^4$ is hydrogen or $C_1$–$C_6$ alkyl; and a is 0, 1 or 2, which process comprises reacting a silane of the formula

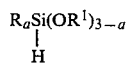

wherein R, $R^1$, and a are as defined above, with an amine of the formula

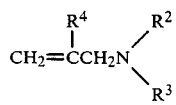

wherein $R^2$, $R^3$ and $R^4$ are as defined above, in the presence of a catalytic amount of a rhodium-triorganophosphorus-complex catalyst comprising rhodium in complex combination with a triorganophosphorus ligand wherein the organo moiety contains from 1 to 18 carbon atoms, to produce the aminopropylalkoxysilane.

Preferable silane starting materials useful in the process of this invention include those wherein a is O and R and $R^1$ are methyl or ethyl. Illustrative of the silanes that can be used in the process of this invention are triethoxysilane, trimethoxysilane, tripropoxysilane, triisopropoxysilane, tributoxysilane, methyldimethoxysilane, ethyldimethoxysilane, methyldiethoxysilane, dimethylmethoxysilane, trioctyloxysilane, methyldioctyloxysilane, dimethyloctyloxysilane, and the like.

Preferable amine starting materials useful in the process of this invention include allylamines wherein $R^2$ and $R^3$ are both hydrogen and $R^4$ is hydrogen or methyl. Illustrative of the amines that can be used in the process of this invention are allylamine, N,N-dimethylallylamine, N,N-diethylallylamine, N-allylaniline, methallylamine, diallylamine, triallylamine, allylethylenediamine, allyldiethylenetriamine, and the like.

The ratio of the silane starting material to amine useful in the process of this invention can be varied from 1.5:1 to 1:1.5 and is preferably in the range of 1.1:1 to 1:1.1.

The rhodium-triorganophosphorus-complex catalysts useful in the process of this invention comprise rhodium in complex combination with a triorganophosphorus ligand wherein each organo moiety is monovalently bonded to the phosphorus atom through a carbon atom or an aliphatic etheric oxygen atom and the phosphorus atom possesses one available pair of electrons. The term "complex" as used in the specification and claims means a coordination compound formed by the union of one or more electronically rich molecules or atoms capable of independent existence with one or more electronically poor molecules or atoms, each of which is also capable of independent existence. The complex may contain additional components besides the rhodium and the ligand, such as hydrogen or carbon monoxide, provided that the additional components have no deleterious effect on the catalytic activity of the complex. Chlorine, for example, may not be an acceptable component of the complex because the addition of chlorine to the hydrosilation reaction mixture could reduce the gamma- to beta-isomer ratio of the aminopropylalkoxysilane end product produced. Certain rhodium-triorganophosphorus-complex catalysts of the type that are utilized in the process of this invention are known. See, e.g. U.S. Pat. Nos. 3,527,809 and 4,148,430.

Regardless of whether the active complex catalyst is preformed prior to introduction into the hydrosilation reaction involved in the process of this invention or whether the active catalyst species is prepared in situ during the hydrosilation reaction, it is preferable that the reaction be effected in the presence of free triorganophosphorus ligand which can be considered, if desired, as a modifier or co-catalyst and/or diluent. By "free triorganophosphorus ligand" is meant the triorganophosphorus compounds that are not complexed with the rhodium atom in the active complex catalyst. It is preferable that at least about 2 equivalents of free triorganophosphorus ligand be present per equivalent of rhodium. More preferably, at least about 10 equivalents of free triorganophosphorus ligand per equivalent of rhodium be employed. Most preferably, at least about 50 equivalents of free triorganophosphorous ligand per equivalent of rhodium be employed. The upper limit on the ligand concentration does not appear to be critical and would be dictated largely by commercial and economic considerations.

Illustrative of the triorganophosphorus ligands which are contemplated in the practice of this invention are trialkylphosphites, triarylphosphites and triarylphosphines. Triarylphosphines are the preferred class of ligands. Illustrative of the ligands which are suitable for forming the complex catalysts are trimethylphosphite, tri-n-butylphosphite, triphenylphosphite, trinaphthylphosphite, triphenylphosphine, trinaphthylphosphine, phenyl diphenylphosphinite, diphenyl phenylphosphonite, tri-(p-methoxyphenyl) phosphite, and the like. Triphenylphosphine is the most preferred ligand.

The preparation of the complex catalysts utilized in the process of this invention is documented in the literature. A suitable method is to combine the rhodium salt of an organic acid with the ligand, e.g., triphenylphosphite, triphenylphosphine, etc., in liquid phase. The valence state of rhodium may then be reduced by hydrogenating the solution prior to the use of the catalysts therein. Alternatively, the catalysts may be prepared from a carbon monoxide complex of rhodium. For example, one could start with dirhodium octacarbonyl, and by heating this substance with the ligand, the ligand will replace one or more of the carbon monoxide molecules, thus producing the desired catalyst. It is also possible to start with the ligand of choice and rhodium metal; or an oxide of rhodium, and prepare the active catalyst species in situ during the hydrosilation reaction. Illustrative of preformed catalysts are rhodium hydridocarbonyl-tris(triphenylphosphine) and rhodium hydrido-tetrakis(triphenylphosphine).

Preparation of the active catalyst in situ can be accomplished, for example, by the addition of rhodium dicarbonyl acetylacetonate, or rhodium carbonyl triphenylphosphine acetylacetonate, and free triphenylphosphine to the hydrosilation reaction mixture, preferably utilizing about 50 equivalents of free triphenylphosphine per equivalent of rhodium.

The hydrosilation reaction involved in the process of this invention can be conducted at room temperature if desired but, as a practical matter, the reaction temperature should be at least about 50° C., preferably between about 100° C. to about 175° C. and most preferably between about 110° C. to about 135° C. The pressure of the reaction is not critical. The reaction can be conducted at atmospheric, sub-atmospheric or super-atmospheric pressure.

The concentration of the rhodium-triorganophosphorus-complex catalyst used in the process of this invention depends on reaction temperature and time but, in general, should be greater than about 5 ppm rhodium, based on the total combined weight of the silane and amine used. The upper limit on the catalyst concentration is not critical and would be determined largely by commercial and economic considerations. Preferably, the catalyst concentration should be in the range of about 40-200 ppm rhodium, and most preferably in the range of about 50-100 ppm rhodium, based on the total combined weight of the silane and amine used.

The reaction time used in the process of this invention will vary depending upon the other conditions, such as amount of catalyst or the reaction temperature. The higher the catalyst concentration and reaction temperature, the shorter the reaction time. In general, when the catalyst concentration is in the range of 50-200 ppm rhodium based on the total combined weight of the silane and amine used and the reaction temperature is between about 110° C. to about 130° C., a reaction time of about 2-5 hours is sufficient although the yield of the reaction is not significantly affected when a longer reaction time, such as 10 hours, is used.

No solvent is necessary for the hydrosilation reaction involved in the process of this invention. If a solvent is desired, suitable solvents are hydrocarbons such as xylene, toluene, tri-isopropylbenzene, and the like.

The aminopropylalkoxysilanes obtained by the process of this invention are useful, for example, as glass-plastic coupling agents, bonding aids, additives to phenolic binder/foundry mixtures, adhesion promoters for vinyl plastisols, polyurethane elastomers, and epoxy and acrylic-based inks. Illustrative of these aminopropylalkoxysilanes are aminopropyltrimethoxysilane, aminopropyltriethoxysilane, aminopropylmethyldimethoxysilane, aminopropyltri-isopropoxysilane, N-phenylaminopropyltriethoxysilane, N-phenylaminopropylmethyldiethoxysilane, tris(triethoxysilylpropyl)amine, bis-(triethoxysilylpropyl)amine, tris-(trimethoxysilylpropyl)amine, bis-(trimethoxysilylpropyl)amine, N-(beta-aminoethyl)aminopropyltriethoxysilane, and the like.

The process of this invention will produce, as reaction products, aminopropylalkoxysilanes wherein the gamma- to beta-isomer ratio is, in general, greater than 15 to 1. The gamma- to beta-isomer ratio achieved utilizing the preferred embodiment of this invention is at least about 25 to 1 and more preferably at least about 50 to 1. This is a significant improvement over the gamma- to beta-isomer ratio ($\leq \sim 15$ to 1) obtained using known methods for the hydrosilation reaction.

The following Examples are presented to more clearly illustrate the process of this invention. The abbreviations and symbols used in the Examples have the following meanings:

| Abbreviation or Symbol | Meaning |
| --- | --- |
| % | Percent by weight |
| g. | grams |
| mg. | milligram |
| cc. | cubic centimeter |
| ml. | milliliter |
| °C. | degrees centigrade |
| ppm | parts by weight per million parts by weight |
| eq. | equivalent |
| GC | gas chromatography |

EXAMPLE 1

Into a 3 cc. Swagelok capped stainless steel tube were added 1 g. (0.006 mole) triethoxysilane, 0.35 g. (0.006 mole) allylamine, 5 g. xylene and the catalyst rhodium hydridocarbonyl-tris-(triphenylphosphine) (100 ppm rhodium, 0.89 mg.) to form a reaction mixture. The reaction mixture so formed was heated to 150° C. in a fluidized sand bath for 10 hours and then cooled to room temperature. Analysis of the product so formed by gas chromatography showed that aminopropyltriethoxysilane had been formed in yields greater than 70% with a gamma- to beta-isomer ratio of 26 to 1.

COMPARATIVE EXAMPLE A

Into a 45 ml. Parr bomb equipped with a pressure gauge were added 0.10 g. of anhydrous Na$_2$CO$_3$, 8.1 g. (0.05 mole) triethoxysilane, 2.9 g. (0.05 mole) allylamine and 15 ppm H$_2$PtCl$_6$. The bomb was placed in a fluidized sand bath which was preheated to 130° C. for 12 hours. The contents of the bomb were then cooled. GC analysis of the product so formed showed that the yield of animopropyltriethoxysilane was greater than 75% and the gamma- to beta-isomer ratio was 4 to 1.

COMPARATIVE EXAMPLE B

The same procedure as described in Comparative Example A was used except that 200 ppm of H$_2$PtCl$_6$ was used as the catalyst. GC analysis showed that the yield of aminopropyltriethoxysilane was greater than 60% with a gamma- to beta-isomer ratio of 6 to 1.

COMPARATIVE EXAMPLE C

The same procedure as described in Comparative Example A was used except that cis-Pt(NH$_3$)$_2$Cl$_2$ (0.0001 g.) was used as the catalyst. GC analysis showed that the yield of aminopropyltriethoxysilane was greater than 60% with a gamma- to beta-isomer ratio of 5 to 1.

EXAMPLE 2

The same procedure as described in Example 1 was used except that rhodium hydridotetrakis-(triphenylphosphine) (100 ppm rhodium) was used as the catalyst. GC analysis showed a yield of aminopropyltriethoxysilane greater than 70% with a gamma- to beta-isomer ratio of 30 to 1.

COMPARATIVE EXAMPLE D

The same procedure as described in Comparative Example A was used, except that 0.0004 g. of platinum tetrakis-(triphenylphosphine) was used as the catalyst. GS analysis showed that the yield of aminopropyltriethoxysilane was greater than 60% and the gamma- to beta-isomer ratio was 4 to 1.

EXAMPLE 3

Into a 3cc. Swagelok capped stainless steel tube were added 1 g. (0.006 mole) triethoxysilane, 0.35 g. (0.006 mole) allylamine, 0.89 mg. (100 ppm rhodium) of the catalyst rhodium hydridocarbonyltris-(triphenylphosphine), and 12.9 mg. triphenylphosphine (50 equivalents triphenylphosphine per equivalent of rhodium) to form a reaction mixture. The reaction mixture so formed was heated to 125° C. in a fluidized sand bath for 4 hours and then cooled to room temperature. GC analysis of the product so formed showed that the yield of aminotriethoxysilane was greater than 70% with a gamma- to beta-isomer ratio of 25 to 1.

EXAMPLE 4

The same procedure as described in Example 3 was used, except that 100 equivalents of triphenylphosphine (51.6 mg.) per equivalent of rhodium was used. GC analysis showed a yield of aminopropyltriethoxysilane was greater than 70% with a gamma- to beta-isomer ratio of 31 to 1.

EXAMPLE 5

The same procedure as described in Example 3 was used, except that 200 equivalents of triphenylphosphine (51.6 mg.) per equivalent of rhodium was added. GC analysis showed a yield of aminopropyltriethoxysilane greater than 70% with a gamma- to beta-isomer ratio of 59 to 1.

EXAMPLE 6

Into a 3 cc. Swagelok capped stainless steel tube were added 1 g. (0.006 mole) trimethoxysilane, 0.35 g. (0.006 mole) allylamine, 0.5 g. xylene, 1.07 mg. (200 ppm rhodium) of the catalyst rhodium hydridocarbonyl- tris-(triphenylphosphine) and 15.3 mg. triphenylphosphine (50 eq./Rh eq.) to form a reaction mixture. The reaction mixture so formed was heated to 110° C. for 4 hours and then cooled to room temperature. GC analysis of the product so formed showed aminopropyltrimethoxysilane had been formed with a gamma- to beta-isomer ratio of greater than 20 to 1.

EXAMPLE 7

A 250 ml. round bottom flask was equipped with a magnetic stirrer and stir bar, standard heating mantle with thermowatch, thermometer, 125 ml. addition funnel, Friedrick's condenser, and N$_2$ inlet/bubbler. The flask was then charged with 82.0 g. (0.499 mole) of triethoxysilane followed by 2.0 g. triphenylphosphine and 0.140 g. of rhodium hydridocarbonyl-tris-(triphenylphosphine). Once the flask and contents were heated to 110° C., a dropwise addition of allylamine was begun. The addition was split into 1 ml. additions spaced 10 minutes apart. The addition was complete in 5 hours for a total of 22.8 g. (0.399 mole) allylamine. An additional hour at 110° C. was maintained as a "cook period" and then the reaction mixture was cooled to room temperature. GC analysis of the product so formed showed a yield of aminopropyltriethoxysilane of greater than 70% with a gamma- to beta-isomer ratio of greater than 25 to 1.

EXAMPLE 8

The same procedure as described in Example 7 was used, except that methyldiethoxysilane was used as the starting silane and the reaction temperature was about 100° C. GC analysis of the product so formed showed that aminopropylmethyldiethoxysilane was formed in a yield greater than 60% with a gamma- to beta-isomer ratio of 28 to 1.

COMPARATIVE EXAMPLE E

The same procedure as described in Comparative Example A was used, except that 8.0 g. (0.06 mole) of methyldiethoxysilane was used as the starting silane and 3.4 g. (0.06 mole) of allylamine was used. GC analysis of the product so formed showed that the yield of aminopropylmethyldiethoxysilane was greater than 70% with a gamma- to beta-isomer ratio of 5 to 1.

EXAMPLE 9

A 100 ml. three-neck round bottom flask was equipped with a magnetic stir bar, standard heating mantel, thermometer, 10 ml. addition funnel, water condenser and N$_2$ inlet/bubbler. The flask was charged with 20 g. (0.122 moles) of triethoxysilane followed by 0.01 g. of rhodium dicarbonyl acetylacetonate (200 ppm rhodium based on triethoxysilane charged), 2.03 g. of triphenylphosphine (200 eq. triphenylphosphine/eq. rhodium) and 20 g. of xylene. The flask and contents were heated to 130° C. and held at 130° C. for 15 minutes. A dropwise addition of allylamine (7.0 g., 0.122 moles) was then conducted over a two hour period with the temperature maintained between 120°–140° C. After heating for an additional hour, the reaction mixture was cooled to room temperature. GC analysis of the product so formed showed that the yield of aminopropyltriethoxysilane was greater than 75% with a gamma- to beta-isomer ratio of greater than 30 to 1.

What is claimed is:

1. A process for preparing an aminopropylalkoxysilane having the formula

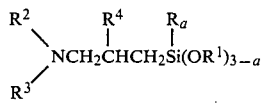

wherein R and $R^1$ individually are $C_1$–$C_6$ alkyl; $R^2$ and $R^3$ individually are hydrogen, $C_1$–$C_{10}$ alkyl, $C_1$–$C_{10}$ alkenyl, —$CH_2CH_2NHCH_2CH_2NH_2$, —$CH_2CH_2NH_2$, phenyl or substituted phenyl; $R^4$ is hydrogen or $C_1$–$C_6$ alkyl; and a is 0, 1 or 2, which process comprises reacting:

a. a silane having the formula

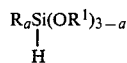

wherein R, $R^1$ and a are as defined above;

b. with an amine having the following formula:

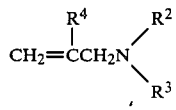

wherein $R^2$, $R^3$ and $R^4$ are as defined above;

c. in the presence of a catalytic amount of a rhodium-triorganophosphorus-complex catalyst comprising rhodium in a complex combination with a triorganophosphorus ligand wherein each organo moiety contains from 1 to 18 carbon atoms, to produce the aminopropylalkoxysilane.

2. A process as recited in claim 1 wherein the triorganophosphorus ligand is trialkylphosphite, triarylphosphite or triarylphosphine.

3. A process as recited in claim 2 wherein the triorganophosphorus ligand is triarylphosphine.

4. A process as recited in claim 3 wherein the triarylphosphine is triphenylphosphine.

5. A process as recited in claim 1 wherein the process is conducted in the presence of at least 2 equivalents of free triorganophosphorus ligand per equivalent of rhodium.

6. A process as recited in claim 5 wherein the process is conducted in the presence of at least 10 equivalents of free triorganophosphorus ligand per equivalent of rhodium.

7. A process as recited in claim 6 wherein the process is conducted in the presence of at least 50 equivalents of free triorganophosphorus ligand per equivalent of rhodium.

8. A process as recited in claim 1 wherein the reaction is conducted at a temperature of about 100° C. to about 175° C.

9. A process as recited in claim 8 wherein the reaction is conducted at a temperature of about 110° C. to about 135° C.

10. A process as recited in claim 1 wherein the rhodium-triorganophosphorus-complex catalyst is present in a concentration of from about 40 to about 200 ppm rhodium based on the total combined weight of the silane and amine.

11. A process as recited in claim 10 wherein the catalyst is present in a concentration of from about 50 to about 100 ppm rhodium based on the total combined weight of the silane and amine.

12. A process as recited in claim 1 wherein the ratio of silane to amine is between 1.5:1 to 1:1.5.

13. A process as recited in claim 1 wherein the ratio of silane to amine is between 1.1:1 to 1:1.1.

14. A process as recited in claim 1 wherein the gamma- to beta-isomer ratio of the aminopropylalkoxysilane produced is at least about 25 to 1.

15. A process as recited in claim 1 wherein the gamma- to beta-isomer ratio of the aminopropylalkoxysilane produced is at least about 50 to 1.

16. A process for preparing an aminopropylalkoxysilane having the formula:

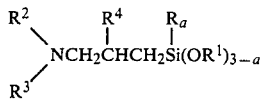

wherein R and $R^1$ individually are $C_1$–$C_4$ alkyl; $R^2$ and $R^3$ individually are hydrogen or $C_1$–$C_4$ alkyl; $R^4$ is hydrogen or methyl; and a is 0, 1 or 2, which process comprises reacting:

a. a silane having the formula

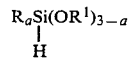

wherein R, $R^1$ and a are as defined above;

b. with an amine having the formula:

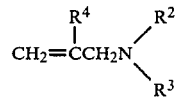

wherein $R^2$, $R^3$ and $R^4$ are as defined above;

c. in the presence of a catalytic amount of a rhodium-triphenylphosphine-complex comprising rhodium in a complex combination with triphenylphosphine; and d. in the presence of free triphenylphosphine, e. at a temperature of at least about 100° C., to produce the aminopropylalkoxysilane.

17. A process as recited in claim 16 wherein a is 0 and R and $R^1$ are methyl or ethyl.

18. A process as recited in claim 17 wherein $R^2$ and $R^3$ are both hydrogen.

19. A process as recited in claim 16 wherein the gamma- to beta-isomer ratio of the aminopropylalkoxysilane produced is at least about 25 to 1.

20. A process as recited in claim 16 wherein the gamma- to beta-isomer ratio of the aminopropylalkoxysilane produced is at least about 50 to 1.

21. A process as recited in claim 16 wherein the process is conducted in the presence of at least 50 equivalents of free triphenylphosphine per equivalent of rhodium.

22. A process as recited in claim 16 wherein the process is conducted at a temperature in the range of from about 100° C. to about 175° C.

23. A process as recited in claim 16 wherein the rhodium-triphenylphosphine-complex catalyst is present in a concentration of from about 50 to about 100 ppm rhodium based on the total combined weight of the silane and amine.

24. A process as recited in claim 16 wherein the catalyst is rhodium hydridocarbonyltris-(triphenylphosphine) or rhodium hydrido-tetrakis (triphenylphosphine).

25. A process as recited in claim 16 wherein the rhodium-triphenylphosphine-complex catalyst is formed by the addition of rhodium dicarbonyl acetylacetonate and free triphenylphosphine to the reaction mixture.

26. A process as recited in claim 25 wherein at least about 50 equivalents of free triphenylphosphine are added per equivalent of rhodium.

27. A process as recited in claim 26 wherein at least about 200 equivalents of free triphenylphosphine are added per equivalent of rhodium.

28. A process as recited in claim 16 wherein the rhodium-triphenylphosphine-complex catalyst is formed by the addition of rhodium carbonyl triphenylphosphine acetylacetonate and free triphenylphosphine to the reaction mixture.

29. A process as recited in claim 28 wherein at least 50 equivalents of free triphenylphosphine are added per equivalent of rhodium.

* * * * *

UNITED STATES PATENT AND TRADEMARK OFFICE
CERTIFICATE OF CORRECTION

PATENT NO. : 4,556,722
DATED : December 3, 1985
INVENTOR(S) : Jennifer M. Quirk and Scot Turner It is certified that error appears in the above-identified patent and that said Letters Patent is hereby corrected as shown below:

In Example 3, column 5, lines 50-51, that portion reading "aminotriethoxysilane" should read --aminopropyltriethoxysilane--.

Signed and Sealed this

Twentieth Day of May 1986

[SEAL]

Attest:

Attesting Officer

DONALD J. QUIGG

Commissioner of Patents and Trademarks